(12) United States Patent
Koike

(10) Patent No.: US 6,999,822 B2
(45) Date of Patent: Feb. 14, 2006

(54) MEDICAL ELECTRODE

(75) Inventor: Yasuaki Koike, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 72 days.

(21) Appl. No.: 10/838,324

(22) Filed: May 5, 2004

(65) Prior Publication Data
US 2004/0225343 A1   Nov. 11, 2004

(30) Foreign Application Priority Data
May 6, 2003  (JP) .......................... P2003-127969

(51) Int. Cl.
A61N 1/18  (2006.01)
A61N 1/36  (2006.01)

(52) U.S. Cl. ...................................... 607/142; 607/152

(58) Field of Classification Search ................ 607/142, 607/152–153; 604/20; 600/385
See application file for complete search history.

(56) References Cited

U.S. PATENT DOCUMENTS

| 5,456,710 | A |   | 10/1995 | Gadsby |
| 5,824,033 | A | * | 10/1998 | Ferrari ........................ 607/142 |
| 5,985,990 | A | * | 11/1999 | Kantner et al. ............. 524/765 |
| 6,019,877 | A |   | 2/2000  | Dupelle et al. |
| 6,330,471 | B1 | * | 12/2001 | Higo et al. .................... 604/20 |
| 6,597,947 | B1 | * | 7/2003  | Inoue et al. .................. 604/20 |
| 6,643,544 | B1 | * | 11/2003 | Adachi et al. ................ 604/20 |

FOREIGN PATENT DOCUMENTS

JP   9-131328 A   5/1997

* cited by examiner

Primary Examiner—Robert Pezzuto
Assistant Examiner—Jason Rosenzweig
(74) Attorney, Agent, or Firm—Sughrue Mion, PLLC

(57) ABSTRACT

A conductive layer is made of a carbon fiber. A conductive lead wire is connected to the conductive layer to lead an electric signal. A conductive gel layer is attached to a first face of the conductive layer and adapted to be adhered on a living body. The conductive gel layer is formed from at least water, polymeric monomer, aminoalcohol as a pH adjuster, and a cross-linking agent so as to have a pH in a range from 8 to 13.

2 Claims, 2 Drawing Sheets

MEDICAL ELECTRODE

BACKGROUND OF THE INVENTION

The present invention relates to a medical electrode to be used for delivering electrical energy to a living body as in the case of a dual-use electrode for use in, e.g., defibrillation and pacing. The present invention also relates to a medical electrode to be used both for delivering a large amount of electrical energy to a living body and for detecting an electrical potential of the living body as in the case of an electrode for use both in, e.g., defibrillation and detection of an electrocardiogram signal.

A conductive layer of the medical electrode is usually formed from a metal plate comprising tin as the main ingredient. In order to reduce impedance existing between the metal plate and the skin of the living body, a conductive gel layer is interposed therebetween. However, in the case of a medical electrode delivered with a large amount of electrical energy, as in the case of an electrode for defibrillation purpose, the conductive gel is subjected to electrolysis, and thus evolves a hydrogen gas and a chlorine gas. These gases collect between the metal plate and the gel layer, causing a change in an electrical characteristic of the electrode or corrosion of the metal plate. Moreover, corrosion of the metal plate, which is induced by an electrolyte (salt) contained in the gel, also arises, which in turn causes a failure.

Japanese Patent Publication No. 10-507651A discloses an electrode comprising a breathable conductive layer, and a gas affinity layer superposed on the conductive layer (cf., pages 7–19 and FIGS. 1–5). As a result, the gas developed in the gel layer passes through the conductive layer and escapes to the outside by way of the gas affinity layer.

However, an electrode using a metal plate as a conductive layer suffers a drawback of corrosion of the conductive layer decreasing in conductivity. Meanwhile, the electrode using carbon for a conductive layer is less apt to corrode and has little chance of decreasing in conductivity. However, restoration of a potential is slow after application of a large defibrillation current, and the electrode suffers a drawback of consumption of much time before the electrode can be used for detecting an electrocardiogram signal.

Standards for a defibrillation electrode include a drop in an electric potential between electrodes to a predetermined voltage level or less within a predetermined period of time after delivery of defibrillation electrical energy.

SUMMARY OF THE INVENTION

It is therefore an object of the invention to provide an electrode capable of leading a bioelectric potential after lapse of a short period of time even when a large amount of electrical energy has been delivered to a living body, without corrosion of a conductive layer.

In order to achieve the above object, according to the invention, there is provided a medical electrode, comprising:
  a conductive layer, comprised of a carbon fiber;
  a conductive lead wire, connected to the conductive layer to lead an electric signal; and
  a conductive gel layer, attached to a first face of the conductive layer and adapted to be adhered on a living body, the conductive gel layer formed from at least water, polymeric monomer, aminoalcohol as a pH adjuster, and a cross-linking agent so as to have a pH in a range from 8 to 13.

Preferably, the medical electrode further comprises an insulating layer, attached to a second face of the conductive layer which is opposite to the first face. The wire is interposed between the insulating layer and the conductive layer while forming a gap communicated to an exterior of the medical electrode.

With such configurations, conductivity of the conductive layer will not be deteriorated, because the conductive layer is resistant to corrosion. Moreover, even after delivering a large amount of electrical energy to a living body, the electrode enables delivery of nominal electrical energy or leading of a biological potential after lapse of a short period of time.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION

Figure 1:
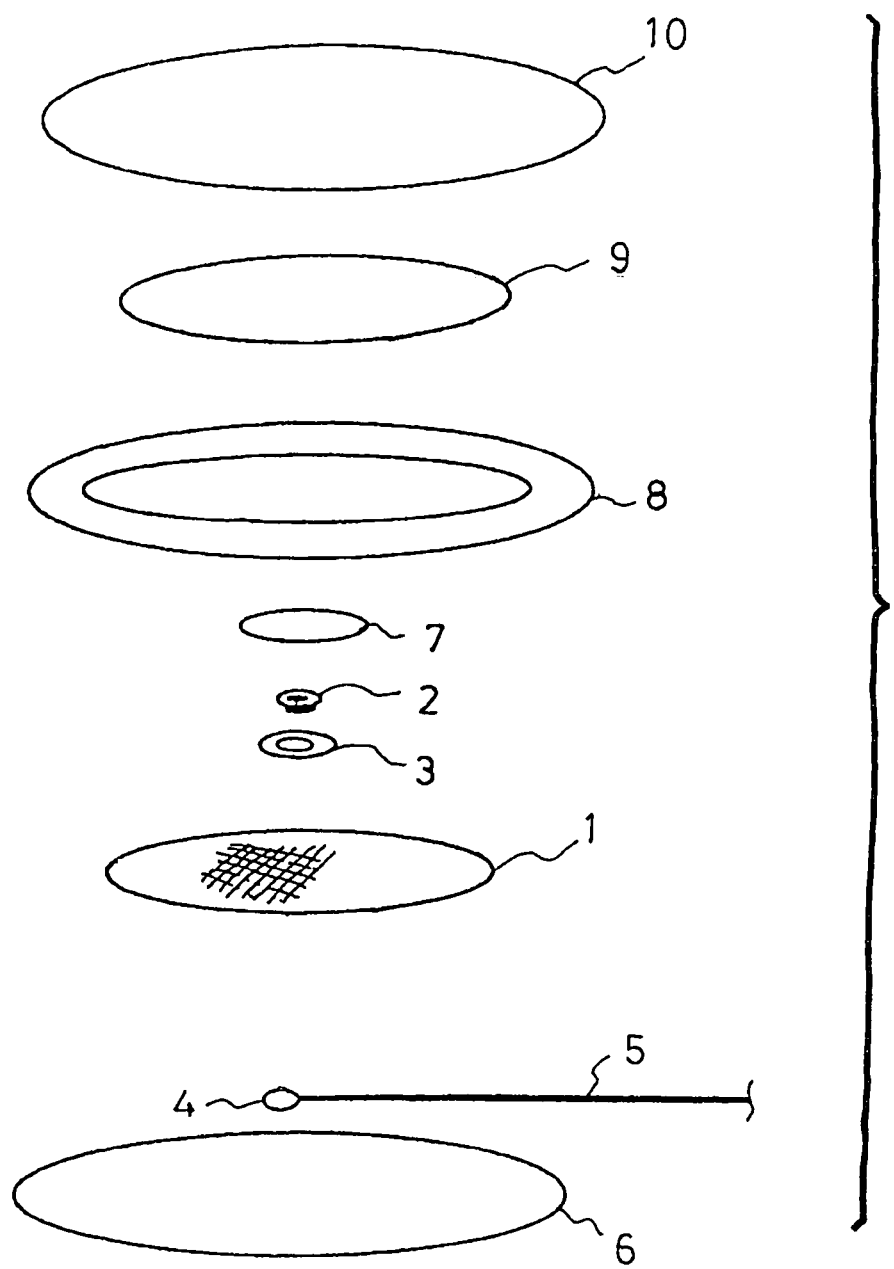
FIG. 1 is an exploded perspective view of a medical electrode according to one embodiment of the invention.

The configuration of a medical electrode according to one embodiment of the invention will be first described with reference to FIG. 1.

A conductive layer 1 is made of carbon fiber and formed from, e.g., a carbon woven fabric cloth or a carbon nonwoven fabric cloth. A connector 4 provided at one end of a lead wire 5 is fastened to the center of a back surface of the conductive layer 1 by an eyelet 2 and a washer 3 disposed on a front surface of the conductive layer 1. The back surface of the conductive layer 1 is bonded to the center of an adhesive surface of an adhesive sheet 6 which is an insulating sheet having a larger outer diameter than the conductive layer 1.

Therefore, a portion of the lead wire 5 is sandwiched between the adhesive sheet 6 and the conductive layer 1, and a remaining portion of the lead wire 5 is led to the outside. For instance, an insulated copper wire is used as the lead wire 5. An insulating shield plate 7 is an adhesive sheet and impervious to water.

The conductive layer 1 is surrounded by an annular sheet 8 bonded to the adhesive sheet 6. The annular sheet 8 is also an adhesive sheet. The annular sheet 8 is substantially identical in outer diameter with the adhesive sheet 6 and substantially identical in inner diameter with the conductive layer 1. An adhesive surface is provided on the side of the annular sheet 8 opposing to the adhesive sheet 6.

A conductive gel layer 9 is so tacky as to adhere to the conductive layer 1. The gel layer 9 is substantially identical in size with the conductive layer 1. The gel layer 9 is covered with a cover sheet 10 which is substantially identical in outer diameter with the adhesive sheet 6 and the annular sheet 8. The cover sheet 10 is provided for protecting and maintaining the quality of the gel layer 9 and is to be peeled off when the medical electrode is attached to a living body.

Figure 2A:
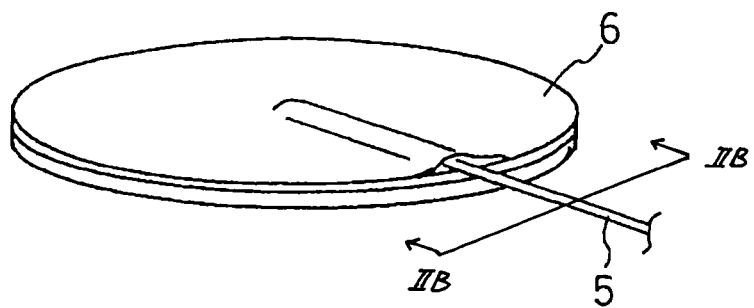
FIG. 2A is a perspective view showing the appearance of the medical electrode of FIG. 1 in an assembled state.
Figure 2B:
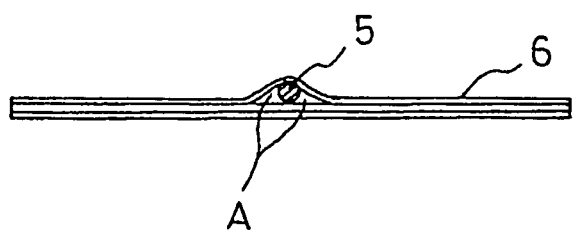
FIG. 2B is a section view of the medical electrode taken along a line IIB—IIB in FIG. 2A.

FIG. 2A shows the appearance of the medical electrode, and FIG. 2B shows the electrode when viewed from the side where the lead wire 5 is led out of the electrode. As shown in FIGS. 2A and 2B, a clearance A is provided between the adhesive sheet 6 and the conductive layer 1 along the lead wire 5. This serves as a channel for leading, to the outside, a gas evolving at the time of use of the medical electrode. It should be noted that the side of the electrode to be attached to the living body is oriented downward to the contrary of FIG. 1.

The conductive gel layer 9 will now be described. The gel layer 9 is manufactured by mixing together water, a polymerization inhibitor, a polymeric monomer, a pH adjuster, and a cross-linking agent; and adding a polymerization initiator to the mixture, to thus initiate polymerization reaction.

Here, aminoalcohol is conductive and also used as a pH adjuster. The pH is adjusted to be 8 to 13.

The reason why the aminoalcohol is used as a pH adjuster is as follows. If, e.g., sodium hydroxide is used as a pH adjuster, sodium ions in the gel layer will be subjected to electrolysis. When the ions have undergone electrolysis, the pH of the vicinity of the conductive layer is changed to alkaline. However, the aminoalcohol does not undergo hydrolysis and hence does not induce a change in the pH.

In a case where carbon has been used for the conductive layer, a stable electric potential is achieved when the gel layer is alkaline rather than being acid. Therefore, the pH of the gel layer of the invention is adjusted to 8 or more. In consideration of influence of the gel layer to skin, the pH is determined to be 13 or less.

By the medical electrode of such a configuration, an electrochemical reaction is unlikely to arise in the gel layer 9 located in the vicinity of the conductive layer 1 even when a large DC current has been caused to flow for defibrillation purpose. As a result, the chance of evolution of a hydrogen gas is lowered. After the large DC current flows, a drop in the electric potential between the electrodes is less obstructed, and restoration of the potential becomes faster, to thus satisfy the existing standards for a defibrillation electrode. Further, the hydrogen gas having been evolved when the large DC current flows is discharged to the outside by way of the clearance A after having passed through the conductive layer 1. This also lowers the chance of the hydrogen gas collecting in the conductive layer 1, thereby preventing obstruction of a drop in the potential between the electrodes. Further, a contact area between the gel and the conductive layer is not reduced.

Table 1 shows weight percentages of respective ingredients of the appropriate gel layer 9. A compounding ratio of water, polymeric monomer, and a pH adjuster for achieving a pH provided on the top row of Table 1 is provided in each column. Here, the pH adjuster is aminoalcohol. The polymerization inhibitor and the cross-linking agent are trace amounts compared with the other components (i.e., a total of 0.2 wt. % or thereabouts), and hence their descriptions are omitted.

TABLE 1

| pH | 13 | 10 | 8 |
|---|---|---|---|
| Water | 32.4 | 43.4 | 43.7 |
| polymeric monomer | 47.2 | 43.0 | 43.3 |
| pH adjuster | 20.2 | 13.4 | 12.8 |

Amounts are in weight percentages (wt %).

Table 2 shows appropriate specific ingredients of the gel layer 9.

TABLE 2

| example No. | 1 | 2 | 3 |
|---|---|---|---|
| pH | 13 | 10 | 8 |
| Ion-exchanged water (water) | 333.9 | 201.0 | 201.0 |
| methoxyphenol (polymerization inhibitor) | 1.0 | 0.6 | 0.6 |
| TBAS (polymeric monomer) | 340.8 | 199.0 | 199.0 |
| monoethanolamine (pH adjuster) | 146.0 | 62.0 | 58.8 |
| methylenebisacrylamide (cross-linking agent) | 0.4 | 0.3 | 0.3 |
| benzoinethylether (polymerization initiator) | 1.8 | 1.8 | 1.8 |

Amounts are in grams (g).

In the above embodiment, monoethanolamine is used as a pH adjuster. However, the same effect can also be yielded in a case where triethanolamine is used as the pH adjuster.

Although the overall shape of the electrode is a circular, the electrode may assume the shape of a rectangular plate or the shape of an oval.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. A medical electrode, comprising:
   a conductive layer, comprised of a carbon fiber;
   a conductive lead wire, connected to the conductive layer to lead an electric signal; and
   a conductive gel layer, attached to a first face of the conductive layer and adapted to be adhered on a living body, the conductive gel layer formed from at least water, polymeric monomer, aminoalcohol as a pH adjuster, and a cross-linking agent so as to have a pH in a range from 8 to 13.

2. The medical electrode as set forth in claim 1, further comprising:
   an insulating layer, attached to a second face of the conductive layer which is opposite to the first face,
   wherein the wire is interposed between the insulating layer and the conductive layer while forming a gap communicated to an exterior of the medical electrode.

* * * * *